United States Patent
Al Ismail et al.

(10) Patent No.: US 10,564,109 B1
(45) Date of Patent: Feb. 18, 2020

(54) SYSTEMS AND METHODS FOR CORE DATA SHIFTING

(71) Applicant: Saudi Arabian Oil Company, Dhahran (SA)

(72) Inventors: Marwah Al Ismail, Sayhat (SA); Mokhles Mezghani, Dhahran (SA); Abdullah Qasem, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/543,734

(22) Filed: Aug. 19, 2019

(51) Int. Cl.
| | |
|---|---|
| *G01N 21/88* | (2006.01) |
| *G01N 21/952* | (2006.01) |
| *G01N 33/24* | (2006.01) |
| *E21B 49/02* | (2006.01) |

(52) U.S. Cl.
CPC ......... *G01N 21/8851* (2013.01); *E21B 49/02* (2013.01); *G01N 21/952* (2013.01); *G01N 33/24* (2013.01)

(58) Field of Classification Search
CPC ....... E21B 49/02; G01N 21/952; G01N 33/24
See application file for complete search history.

(56) References Cited

U.S. PATENT DOCUMENTS

| | | | |
|---|---|---|---|
| 4,542,648 A | | 9/1985 | Vinegar et al. |
| 5,012,674 A | * | 5/1991 | Millheim ............... E21B 49/02 |
| | | | 324/201 |
| 5,109,697 A | * | 5/1992 | Millheim ............... E21B 49/02 |
| | | | 175/50 |
| 5,581,024 A | | 12/1996 | Meyer, Jr. et al. |
| 6,876,721 B2 | | 4/2005 | Siddiqui |
| 7,983,885 B2 | | 7/2011 | Suarez-Rivera et al. |
| 8,577,614 B2 | | 11/2013 | Norris et al. |
| 8,725,477 B2 | | 5/2014 | Zhang et al. |
| 10,198,804 B2 | | 2/2019 | Sungkorn et al. |
| 2007/0061079 A1 | | 3/2007 | Hu |
| 2009/0080705 A1 | * | 3/2009 | Orpen .................... G01N 33/24 |
| | | | 382/109 |

OTHER PUBLICATIONS

Haralick, Robert M. et al.; "Textural Features for Image Classification" IEEE Transactions on Systems, Man, and Cybernetics, vol. SMC-3, No. 6, Nov. 1973; pp. 610-621.

* cited by examiner

*Primary Examiner* — Edward Park
(74) *Attorney, Agent, or Firm* — Bracewell LLP; Constance G. Rhebergen; Christopher L. Drymalla (57) ABSTRACT

Provided are systems and methods for shifting core data to account for flaws that include segmenting core data into multiple contiguous core segments defined by breaking points and iteratively assessing and shifting the segments in sequence (from the deepest segment to the shallowest segment) to align the core data of the contiguous core segments with corresponding segments of log data. For each shift of an assessed segment by a given distance the shallower segments of core data are shifted by the given distance. The breaking points used to define contiguous core segments are identified based on image processing of an image of the core, including identification and comparison of Haralick textual feature parameters across different portions of the core image.

24 Claims, 7 Drawing Sheets

SYSTEMS AND METHODS FOR CORE DATA SHIFTING

FIELD

Embodiments relate generally to developing wells, and more particularly to well assessment and operation.

BACKGROUND

A well generally includes a wellbore (or "borehole") that is drilled into the earth to provide access to a geologic formation below the earth's surface (or "subsurface formation"). A well may facilitate the extraction of natural resources, such as hydrocarbons and water, from a subsurface formation, facilitate the injection of substances into the subsurface formation, or facilitate the evaluation and monitoring of the subsurface formation. In the petroleum industry, hydrocarbon wells are often drilled to extract (or "produce") hydrocarbons, such as oil and gas, from subsurface formations.

Developing a hydrocarbon well for production typically involves several stages, including a drilling stage, a completion stage and a production stage. The drilling stage involves drilling a wellbore into a portion of the formation expected to contain hydrocarbons (often referred to as "hydrocarbon reservoir" or "reservoir"). The drilling process is usually facilitated by a drilling rig that sits at the earth's surface and that facilitates a variety of operations, such as operating a drill bit to cut the wellbore. The completion stage involves operations for making the well ready to produce hydrocarbons, such as installing casing, perforating the casing, installing production tubing, installing downhole valves for regulating production flow, or pumping fluids into the well to fracture, clean or otherwise prepare the reservoir and well to produce hydrocarbons. The production stage normally involves producing hydrocarbons from the reservoir by way of the well. During the production stage, the drilling rig is typically replaced with valves that can be operated, for example, to regulate pressure in the wellbore, to control production flow from the wellbore, or to provide access to the wellbore. An outlet valve is often connected to a distribution network of midstream facilities, such as tanks, pipelines or transport vehicles that transport the production to downstream facilities, such as refineries or export terminals.

The various stages of developing a hydrocarbon well often include challenges that are addressed to successfully develop the well. For example, in an effort to accurately characterize a well, a well operator may conduct coring operations to extract and collect cores from the well. The cores may be assessed to identify characteristics of the well (and the surrounding formation) at corresponding depths, and the characteristics may be assembled to generate core-logs that characterize the well and the surrounding formation at different depths.

SUMMARY

Collection and assessment of samples of formation rock (or "core samples" or "cores") can be an important aspect of successfully and efficiently developing a hydrocarbon well. For example, cores may enable geoscientists to directly assess properties of the formation rock, such as density, porosity, permeability, wettability, organic matter content and fluid content, in a laboratory. This information can be used, for example, to calibrate well log data obtained by way of well logging operations, to generate geological models of the subsurface formation, or to determine well location, drilling or operating parameters.

When cores are extracted from a borehole they are typically associated with a "driller" depth (or "core" or "lab" depth), which is determined at the drill site, as the cores are extracted from the wellbore. Unfortunately, the driller depth may not correspond to the actual depth (or "true depth") from which the core was extracted. This can make it difficult to map data associated with a core (or "core data") to data that tracks the true depth, such as data obtained by way of well logging (or "log data"). In the case of an extracted core, discrepancies between the driller depth and the true depth is often attributable to flaws in the core, such as missing sections (or "no recovery zones") or the breakdown of the core into small fragments (or "rubble zones") that occur at various points along the core. In many instances, flaws cause portions of the core to physically shift relative to one another during collection, which can, in turn, cause the associated driller depth for the portions to skew (or "offset") from the true depth.

Techniques to account for differences between driller depth and true depth typically apply a single shift to the core data. Although, a single shift may account for a single flaw, it may not account for multiple flaws that cause sections to be offset by different distances. For example, a first segment of a core may be offset by a first distance, with a second segment offset by a second distance. In such an instance, shifting all of the core data by the first distance may align the first segment of core data with its corresponding segment of log data; however, the second segment may remain offset from its corresponding segment of the log data.

Recognizing shortcomings of existing techniques for correcting core data, provided are systems and methods for shifting core data to account for flaws. In some embodiments core data is segmented into multiple contiguous core segments defined by breaking points, and the segments are iteratively assessed and shifted in sequence (for example, from the deepest segment to the shallowest segment) to align the core data of the contiguous core segments with corresponding segments of log data. In some embodiments, for each shift of an assessed segment by a given distance, all shallower segments of core data are shifted by the given distance. In some embodiments, the breaking points used to define contiguous core segments are identified based on image processing of an image of the core (or a "core image"). The image processing may include, for example, identification and comparison of Haralick textual feature parameters across different portions of the core image.

Provided in some embodiments is a method of core data shifting. The method including: obtaining a core image representing a length of a core extracted from a wellbore of a well extending into a formation, the core including a sample of rock of the formation extracted from the wellbore; determining, based on the core image, breaking points along the length of the core, each of the breaking points defining a location of a flaw within the core; determining, based on the breaking points, contiguous core segments of the core; determining, for each of the contiguous core segments of the core, a core depth interval for the contiguous core segment; generating, based on the contiguous core segments of the core, a shifted core-log, the generating of the shifted core-log including iteratively assessing each of the contiguous core segments in series from the contiguous core segment associated with a deepest core depth interval to the contiguous core segment associated with a shallowest core depth interval, the assessment of each of the contiguous core segments including: determining a current core depth interval for the contiguous core segment, the core depth interval for the contiguous core segment including the core depth interval currently associated with the contiguous core segment; correlating the core data for the contiguous core segment to log data for a log depth interval corresponding to the core depth interval currently associated with the contiguous core segment to identify a segment of the log data corresponding to the core data for the contiguous core segment; determining, based on the segment of the log data identified, an offset distance for the contiguous core segment, the offset distance for the contiguous core segment including an offset distance between the core depth interval for the contiguous core segment and the log depth interval associated with the segment of the log data identified; determining, based on the offset distance for the contiguous core segment, a shifted core depth interval for the contiguous core segment, the shifted core depth interval corresponding to a shift of the core depth interval currently associated with the contiguous core segment by the offset distance for the contiguous core segment; and for each of the contiguous core segments having a core depth interval that is associated with depths shallower than the core depth interval of the contiguous core segment, shifting the core depth interval associated with the contiguous core segment by the offset distance; the shifted core-log associating core data for each contiguous core segment of the contiguous core segments with the shifted depth interval determined for the contiguous core segment.

In some embodiments, each of the flaws corresponds to a no recovery zone or a rubble zone within the core. In some embodiments, determining breaking points along the length of the core includes comparison of Haralick textual feature parameters across different portions of the core image. In some embodiments, a beginning or end of each of the contiguous core segments is defined by one of the breaking points. In some embodiments, the log depth interval corresponding to the core depth interval includes a depth interval that includes and is larger than the core depth interval. In some embodiments, the method further includes developing a reservoir in the formation based on the shifted core-log. In some embodiments, developing the reservoir in the formation based on the shifted core-log includes identifying operating parameters for the hydrocarbon well based on the shifted core-log, and operating the well in accordance with the operating parameters. In some embodiments, developing the reservoir in the formation based on the shifted core-log includes generating a model of the reservoir based on based on the shifted core-log.

Provided in some embodiments is a hydrocarbon well drilling system that includes the following: a drilling system adapted to extract a core from a wellbore of a well extending into a formation, the core including a sample of rock of the formation; and a well control system adapted to perform the following operations: obtain a core image representing a length of the core; determine, based on the core image, breaking points along the length of the core, each of the breaking points defining a location of a flaw within the core; determine, based on the breaking points, contiguous core segments of the core; determine, for each of the contiguous core segments of the core, a core depth interval for the contiguous core segment; generate, based on the contiguous core segments of the core, a shifted core-log, the generating of the shifted core-log including iteratively assessing each of the contiguous core segments in series from the contiguous core segment associated with a deepest core depth interval to the contiguous core segment associated with a shallowest core depth interval, the assessment of each of the contiguous core segments including: determining a current core depth interval for the contiguous core segment, the core depth interval for the contiguous core segment including the core depth interval currently associated with the contiguous core segment; correlating the core data for the contiguous core segment to log data for a log depth interval corresponding to the core depth interval currently associated with the contiguous core segment to identify a segment of the log data corresponding to the core data for the contiguous core segment; determining, based on the segment of the log data identified, an offset distance for the contiguous core segment, the offset distance for the contiguous core segment including an offset distance between the core depth interval for the contiguous core segment and the log depth interval associated with the segment of the log data identified; determining, based on the offset distance for the contiguous core segment, a shifted core depth interval for the contiguous core segment, the shifted core depth interval corresponding to a shift of the core depth interval currently associated with the contiguous core segment by the offset distance for the contiguous core segment; and for each of the contiguous core segments having a core depth interval that is associated with depths shallower than the core depth interval of the contiguous core segment, shifting the core depth interval associated with the contiguous core segment by the offset distance; the shifted core-log associating core data for each contiguous core segment of the contiguous core segments with the shifted depth interval determined for the contiguous core segment.

In some embodiments, each of the flaws corresponds to a no recovery zone or a rubble zone within the core. In some embodiments, determining breaking points along the length of the core includes comparison of Haralick textual feature parameters across different portions of the core image. In some embodiments, a beginning or end of each of the contiguous core segments is defined by one of the breaking points. In some embodiments, the log depth interval corresponding to the core depth interval includes a depth interval that includes and is larger than the core depth interval. In some embodiments, the operations further include developing a reservoir in the formation based on the shifted core-log. In some embodiments, developing the reservoir in the formation based on the shifted core-log includes identifying operating parameters for the hydrocarbon well based on the shifted core-log, and operating the well in accordance with the operating parameters. In some embodiments, developing the reservoir in the formation based on the shifted core-log includes generating a model of the reservoir based on based on the shifted core-log.

Provided in some embodiment is a non-transitory computer readable storage medium including program instructions stored thereon that are executable by a processor to perform the following operations for core data shifting: obtaining a core image representing a length of a core extracted from a wellbore of a well extending into a formation, the core including a sample of rock of the formation; determining, based on the core image, breaking points along the length of the core, each of the breaking points defining a location of a flaw within the core; determining, based on the breaking points, contiguous core segments of the core; determining, for each of the contiguous core segments of the core, a core depth interval for the contiguous core segment; generating, based on the contiguous core segments of the core, a shifted core-log, the generating of the shifted core-log including iteratively assessing each of the contiguous core segments in series from the contiguous core segment associated with a deepest core depth interval to the contiguous core segment associated with a shallowest core depth interval, the assessment of each of the contiguous core segments including: determining a current core depth interval for the contiguous core segment, the core depth interval for the contiguous core segment including the core depth interval currently associated with the contiguous core segment; correlating the core data for the contiguous core segment to log data for a log depth interval corresponding to the core depth interval currently associated with the contiguous core segment to identify a segment of the log data corresponding to the core data for the contiguous core segment; determining, based on the segment of the log data identified, an offset distance for the contiguous core segment, the offset distance for the contiguous core segment including an offset distance between the core depth interval for the contiguous core segment and the log depth interval associated with the segment of the log data identified; determining, based on the offset distance for the contiguous core segment, a shifted core depth interval for the contiguous core segment, the shifted core depth interval corresponding to a shift of the core depth interval currently associated with the contiguous core segment by the offset distance for the contiguous core segment; and for each of the contiguous core segments having a core depth interval that is associated with depths shallower than the core depth interval of the contiguous core segment, shifting the core depth interval associated with the contiguous core segment by the offset distance; the shifted core-log associating core data for each contiguous core segment of the contiguous core segments with the shifted depth interval determined for the contiguous core segment.

In some embodiments, each of the flaws corresponds to a no recovery zone or a rubble zone within the core. In some embodiments, determining breaking points along the length of the core includes comparison of Haralick textual feature parameters across different portions of the core image. In some embodiments, a beginning or end of each of the contiguous core segments is defined by one of the breaking points. In some embodiments, the log depth interval corresponding to the core depth interval includes a depth interval that includes and is larger than the core depth interval. In some embodiments, the operations further include developing a reservoir in the formation based on the shifted core-log. In some embodiments, developing the reservoir in the formation based on the shifted core-log includes identifying operating parameters for the hydrocarbon well based on the shifted core-log, and operating the well in accordance with the operating parameters. In some embodiments, developing the reservoir in the formation based on the shifted core-log includes generating a model of the reservoir based on based on the shifted core-log.

While this disclosure is susceptible to various modifications and alternative forms, specific embodiments are shown by way of example in the drawings and will be described in detail. The drawings may not be to scale. It should be understood that the drawings and the detailed descriptions are not intended to limit the disclosure to the particular form disclosed, but are intended to disclose modifications, equivalents, and alternatives falling within the scope of the present disclosure as defined by the claims.

DETAILED DESCRIPTION

Described are embodiments of novel systems and methods for shifting core data to account for flaws. In some embodiments core data is segmented into multiple contiguous core segments defined by breaking points, and the segments are iteratively assessed and shifted in sequence (for example, from the deepest segment to the shallowest segment) to align the core data of the contiguous core segments with corresponding segments of log data. In some embodiments, for each shift of an assessed segment by a given distance, all shallower segments of core data are shifted by the given distance. In some embodiments, the breaking points used to define contiguous core segments are identified based on image processing of an image of the core (or a "core image"). The image processing may include, for example, identification and comparison of Haralick textual feature parameters across different portions of the core image. Although certain embodiments are described in the context of developing hydrocarbon wells, the techniques described may be applied in other context, such as in the development of water wells and other types of wells.

Figure 1:
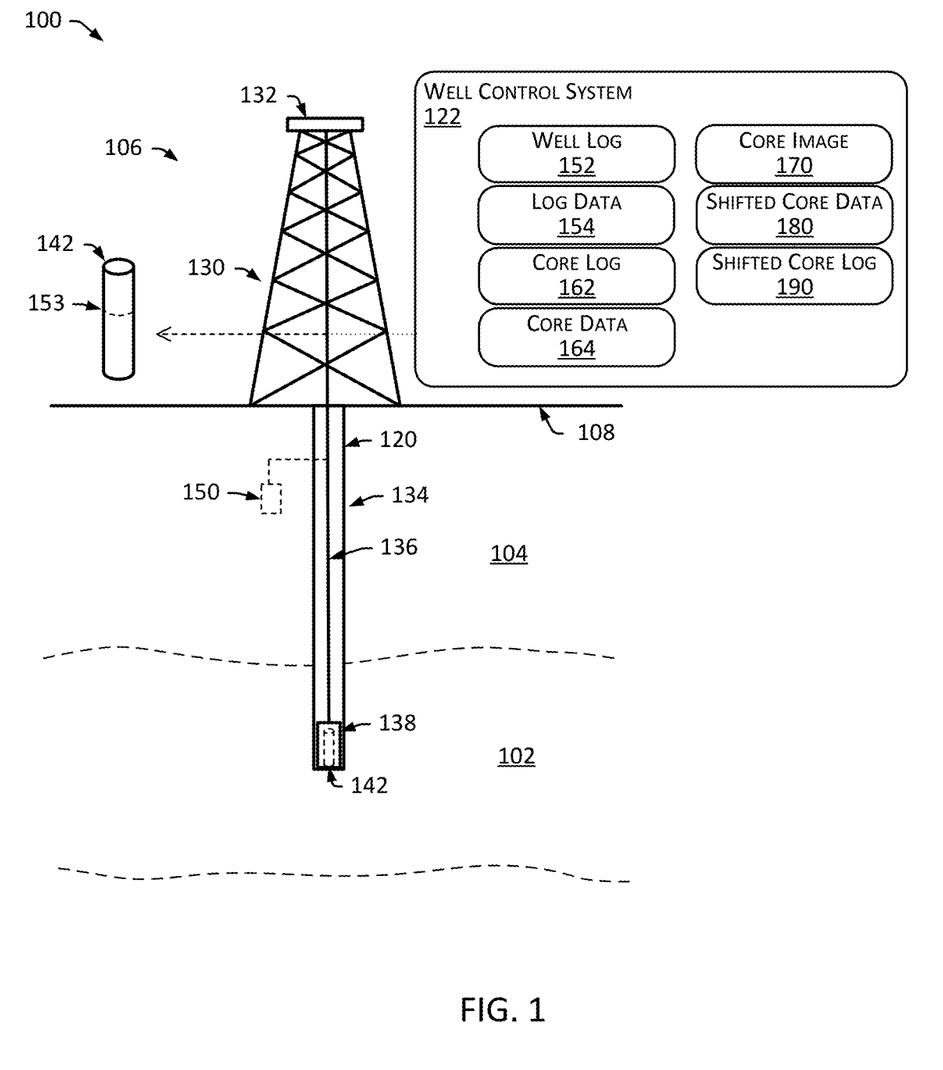
FIG. 1 is diagram that illustrates a well environment in accordance with one or more embodiments.

FIG. 1 is a diagram that illustrates a well environment 100 in accordance with one or more embodiments. In the illustrated embodiment, the well environment 100 includes a reservoir ("reservoir") 102 located in a subsurface formation ("formation") 104 and a well system ("well") 106.

The formation 104 may include a porous or fractured rock formation that resides underground, beneath the Earth's surface (or "surface") 108. The reservoir 102 may be a hydrocarbon reservoir, and the well 106 may be a hydrocarbon well, such as an oil well. In the case of the well 106 being a hydrocarbon well, the reservoir 102 may be a hydrocarbon reservoir defined by a portion of the formation 104 that contains (or that is at least determined to or expected to contain) a subsurface pool of hydrocarbons, such as oil and gas. The formation 104 and the reservoir 102 may each include different layers of rock having varying characteristics, such as varying degrees of density, permeability, porosity, and fluid saturations. In the case of the well 106 being operated as a production well, the well 106 may facilitate the extraction of hydrocarbons (or "production") from the reservoir 102. In the case of the well 106 being operated as an injection well, the well 106 may facilitate the injection of substances, such as gas or water, into the reservoir 102. In the case of the well 106 being operated as a monitoring well, the well 106 may facilitate the monitoring of various characteristics of the formation 104 or the reservoir 102, such as reservoir pressure or saturation.

The well 106 may include a wellbore 120, a well control system (or "control system") 122 and a drilling system 130. The control system 122 may control various operations of the well 106, such as well drilling operations, well completion operations, well production operations or well or formation monitoring operations. In some embodiments, the control system 122 includes a computer system that is the same as or similar to that of computer system 1000 described with regard to at least FIG. 8.

The wellbore 120 (or "borehole") may include a bored hole that extends from the surface 108 into a target zone of the formation 104, such as the reservoir 102. An upper end of the wellbore 120, at or near the surface 108, may be referred to as the "up-hole" end of the wellbore 120. A lower end of the wellbore 120, terminating in the formation 104, may be referred to as the "down-hole" end of the wellbore 120. The wellbore 120 may provide for the circulation of drilling fluids during drilling operations, the flow of hydrocarbons (for example, oil and gas) from the reservoir 102 to the surface 108 during production operations, the injection of substances (for example, water) into the formation 104 or the reservoir 102 during injection operations, or the communication of monitoring devices (for example, logging tools) into the formation 104 of the reservoir 102 during monitoring operations (for example, during in situ well logging operations).

The wellbore 120 may be created, for example, by the drilling system 130 boring through the formation 104. In some embodiments, the drilling system 130 includes a drilling rig 132 and a drill string 134. The drill string 134 may include a drill pipe 136 and a bit 138. In some embodiments, the bit 138 includes a cutting drill bit having rotating teeth that can bore through the formation 104 to create the wellbore 120. In some embodiments, the bit 138 includes a coring bit that can cut into the formation 104 to create samples of formation rock (or "core samples" or "cores") 142 and extract them from the wellbore 120.

Figure 2:
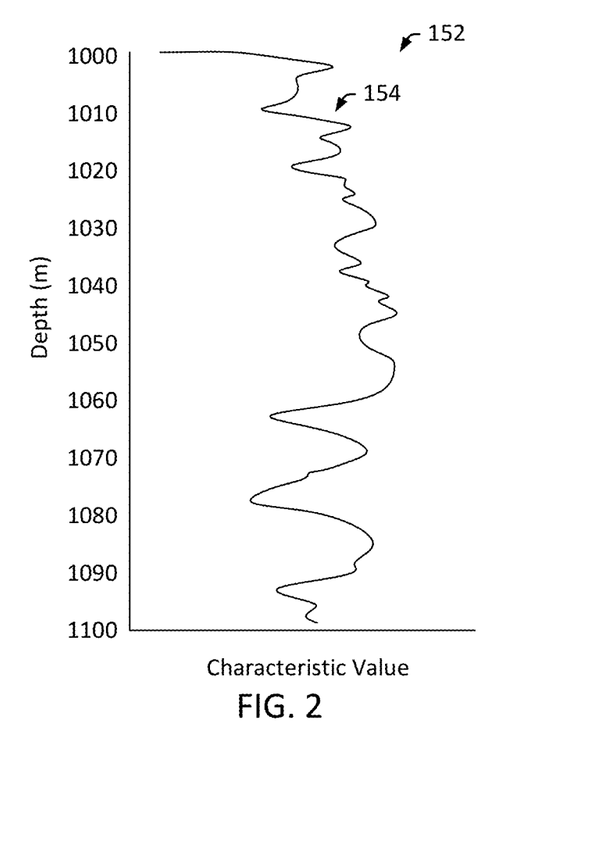
FIG. 2 is diagram that illustrates a well log in accordance with one or more embodiments.

In some embodiments, drilling or completion operations for the well 106 include a well logging operation to generate of a well log 152 for the well 106. A well log 152 for the well 106 may include a record identifying characteristics of the wellbore 120 of the well 106 (or the formation 104 surrounding the wellbore 120) versus depth in the wellbore 120, determined based on log data 154 obtained by way of a logging of the well 106. A well log 152 may include, for example, an acoustic log, a sonic log, a resistivity log, borehole image log, a porosity log, a permeability log, or a nuclear magnetic resonance (NMR) log. A well logging (or "down hole well logging" or "in-situ logging") of the well 106 may include lowering a well logging tool 150 (including sensors) into the wellbore 120 and operating the logging tool 150 to measure (or "log") (using the sensors) characteristics of the wellbore 120 as the logging tool 150 is moved along a length (or "interval") of the wellbore 120. For example, a logging of the well 106 may include lowering a sonic logging tool 150 into the wellbore 120 and, as the logging tool 150 is moved across a depth interval of the wellbore 120 (for example, from a depth of 1000 meters (m) to a depth of 1100 m in the wellbore 120), operating an acoustic source of the sonic logging tool 150 to emit sound waves and operating acoustic sensors of the sonic logging tool 150 to detect corresponding reflections. The difference between the emission and detection times can be used, for example, to determine acoustic travel times within the formation 104, and the acoustic travel times may be used to determine characteristics of the formation 104, such as formation porosity. The measurements or determined characteristics may be recorded in a corresponding well log 152 that provides a mapping of the measurements (or determined characteristics) versus depth in the wellbore 120. For example, a well log 152 for the well 106 may include a mapping of the acoustic travel time (or the corresponding porosity determined) versus depth in the wellbore 120. FIG. 2 is a diagram that illustrates an example well log 152 in accordance with one or more embodiments. In the illustrated embodiment, the well log 152 includes log data 154 that identifies varying values of a characteristic (for example, porosity) of the formation 104 surrounding the wellbore 120 versus depth (for example, from about 1000 m to about 1100 m) in the wellbore 120.

In some embodiments, drilling operations for the well 106 include a coring operation that provides for extraction of one or more cores 142 from the wellbore 120. During a coring operation, a coring bit 138 may be advanced in the wellbore 120 to cut and extract a core 142 from the formation 104. The core 142 may be, for example, a solid cylindrical continuous section of rock of the formation 104, often referred to as a "conventional core" or a "whole core." In such an embodiment, the coring bit 138 may be a hollow cylindrical bit that is lowered into engagement with rock of the formation 104 at a down-hole end of the wellbore 120 and that is rotated (for example, by way of rotation of the drill pipe 136 of the drill string 134) to cut and retrieve the solid cylinder of the rock of the formation 104 from the wellbore 120. In many instances, a retrieved core 142 may have flaws 153, such as missing sections (or "no recovery zones") or the breakdown of the rock of the core 142 into small fragments (or "rubble zones") that occur at various points along the core 142.

Figure 3:
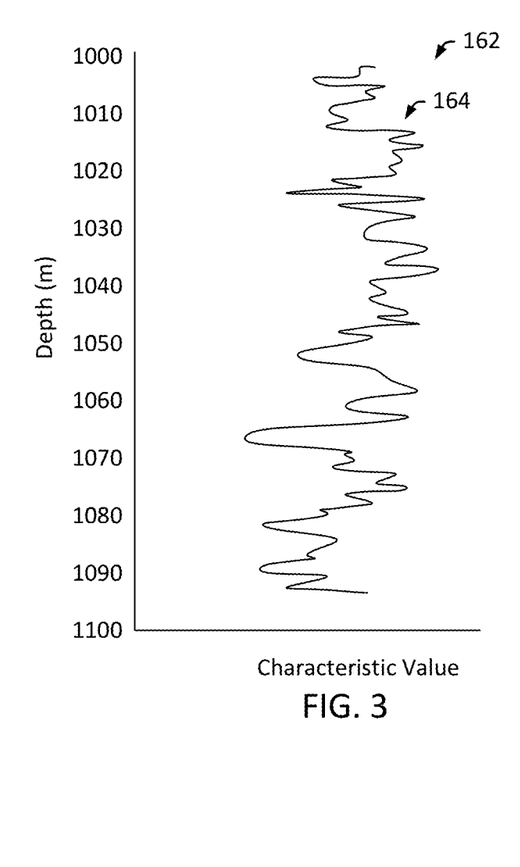
FIG. 3 is diagram that illustrates a core log in accordance with one or more embodiments.

In some embodiments, a core 142 is transported to a laboratory for assessment. Laboratory assessment of a core 142 may include conducting tests on the core 142 in a laboratory environment to identify characteristics of the core 142. The characteristics may include, for example, density, porosity, permeability, fluid saturation, grain density, lithology or texture. In some embodiments, the characteristics identified are used to generate a core log 162 for the well 106. A core log 162 for the well 106 may include a record identifying characteristics of the wellbore 120 of the well 106 (or the formation 104 surrounding the wellbore 120) versus depth in the wellbore 120 that are determined based on core data 164 obtained by way of laboratory assessment of one or more cores 142 extracted from the well 106. For example, a core log 162 for the well 106 may include a mapping of porosity values versus depth in the wellbore 120 determined by way of laboratory assessment of the core 142. In some embodiments, the core data 164 is generated using a single core 142 extracted from a depth interval represented by the core data 164. For example, a 5 m core 142 may be extracted from a depth interval of 100 m to 105 m within the wellbore 120, the extracted core 142 may be transported to a laboratory where it is subjected to tests to determine respective values of porosity across the five meter length of the core 142, and the respective values of porosity may be recorded in a core-log 164 that maps the varying values of porosity across the depth interval of 100 m to 105 m in the wellbore 120. In some embodiments, the core data 164 is generated using multiple cores 142 extracted from a depth interval represented by the core data 164. For example, multiple cores 142 may be extracted from within the depth interval of 100 m to 200 m within the wellbore 120, the extracted cores 142 may be transported to a laboratory where they are subjected to tests to determine respective values of porosity across the length of each core 142, and the respective values of porosity across the lengths of the cores 142 may be assembled and recorded in a core log 162 that maps the varying values of porosity across the depth interval of 100 m to 200 m in the wellbore 120. FIG. 3 is a diagram that illustrates an example core log 162 in accordance with one or more embodiments. The core log 162 includes core data 164 that identifies varying values of a characteristic (for example, porosity) of the formation 104 surrounding the wellbore 120 versus depth (for example, from about 1002 m to about 1092 m) in the wellbore 120.

In some embodiments, the depths associated with a core 142 (and thus the depths associated with corresponding core data 164) are determined based on depths determined at the drill site, as the core 142 is extracted from the wellbore 120. These depths are often referred to as "driller" depths (or "core" or "lab" depths). For example, in extracting a 5 m long core 142 from the wellbore 120, the driller may measure a 100 m distance the coring bit 138 travels into the wellbore 120 before engaging rock of the formation 104, operate the coring bit 138 to cut 5 m into the rock of the formation 104 to cut a solid cylinder of rock of the formation 104 that defines the core 142, retrieve the coring bit 138 (with the core 142) from the wellbore 120, and remove the core 142 from the coring bit 138 at the surface 108. The driller may determine a top (or "starting") core depth of 100 m for the core 142 (the distance the coring bit 150 traveled into the wellbore 120 before engaging the rock of the formation 104), a core length of 5 m, and a bottom (or "end") core depth of 105 m for the core 142 (the sum of the top depth and the length of the core 142). In such an embodiment, the core 142 may be associated with a core depth interval of 100 m to 105 m. Unfortunately, core depths are often skewed from the actual (or "true") depths in the wellbore 120. This can be attributable to inaccuracies of the tools and techniques used for coring operations or to flaws 153 within the cores 142. A flaw 153 may cause portions of the core 142 to shift relative to one another as the core 142 is cut, retrieved or transported, which can, in turn, cause the core depths to skew from actual depths. For example, a 5.0 m long core 142 having rubble zones in-situ may be compacted down to a length of 4.7 m during cutting and extraction of the core 142. This can cause the core depths associated with the core 142 to skew from the actual depths of the core 142 in-situ. As described here, in some embodiments, core data 164 may be shifted to account for discrepancies between core depths and actual depths.

Figure 4A:
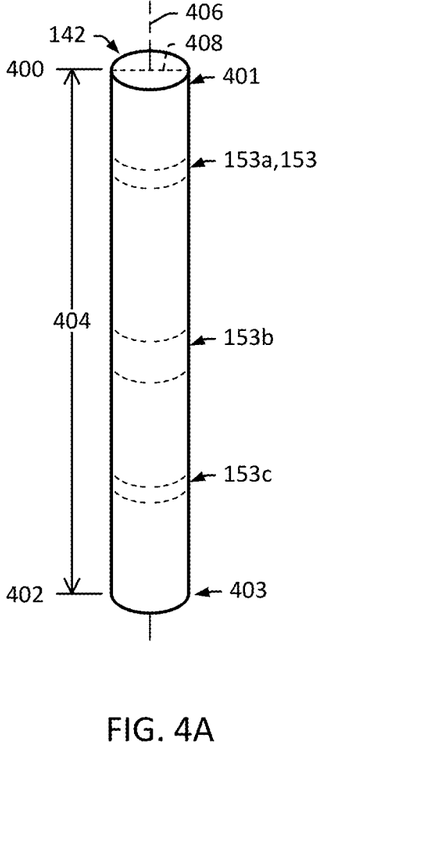
FIG. 4A is diagram that illustrates a core in accordance with one or more embodiments.
Figure 4B:
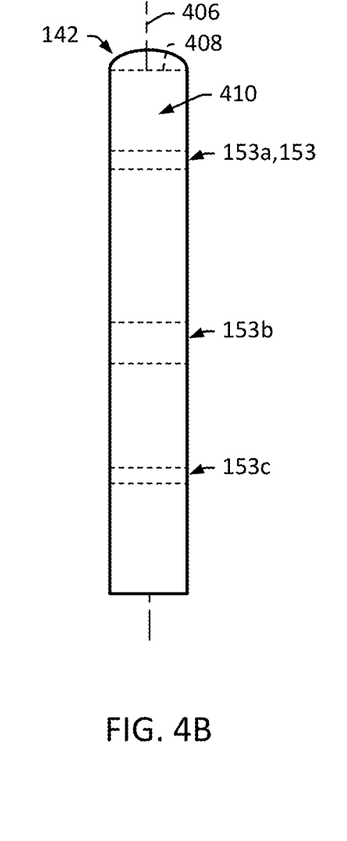
FIG. 4B is diagram that illustrates a sectioned core in accordance with one or more embodiments.
Figure 4C:
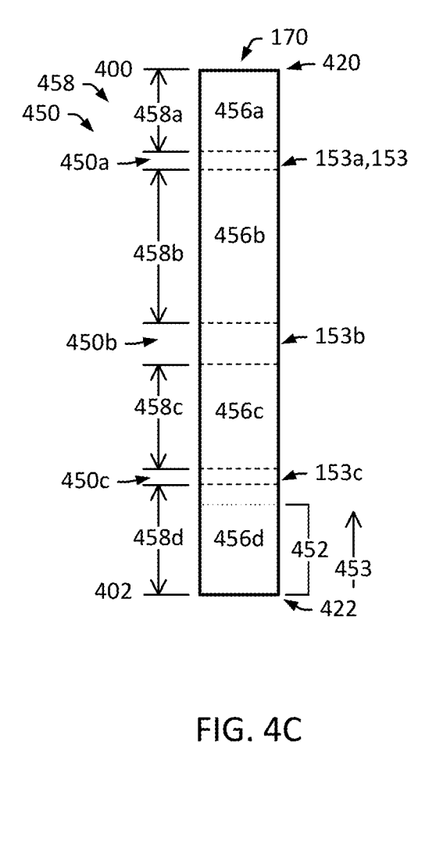
FIG. 4C is diagram that illustrates a core image in accordance with one or more embodiments.
Figure 5A:
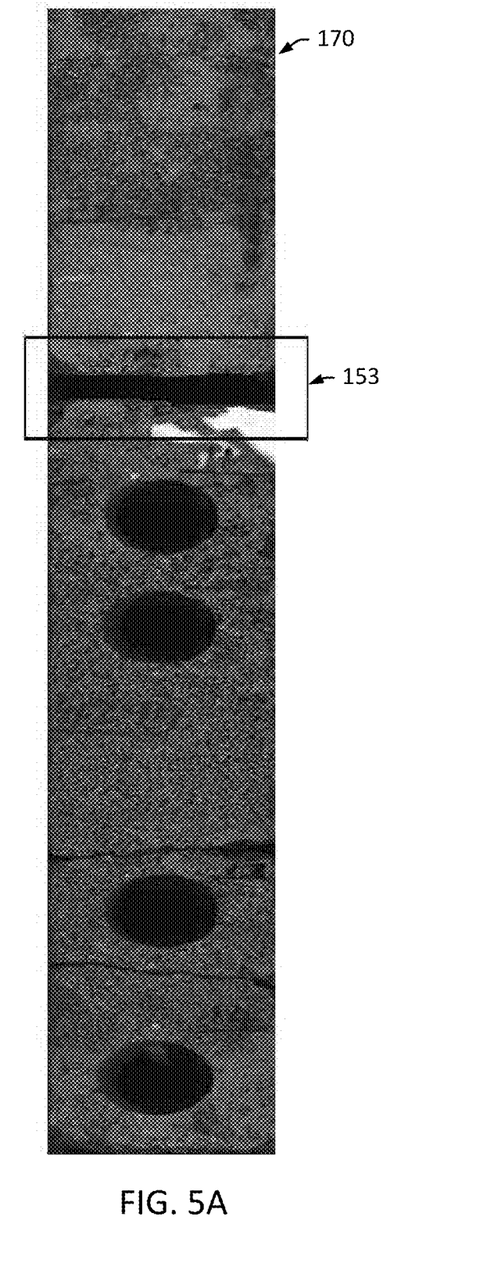
FIGS. 5A and 5B are diagrams that illustrate example core images in accordance with one or more embodiments.
Figure 5B:
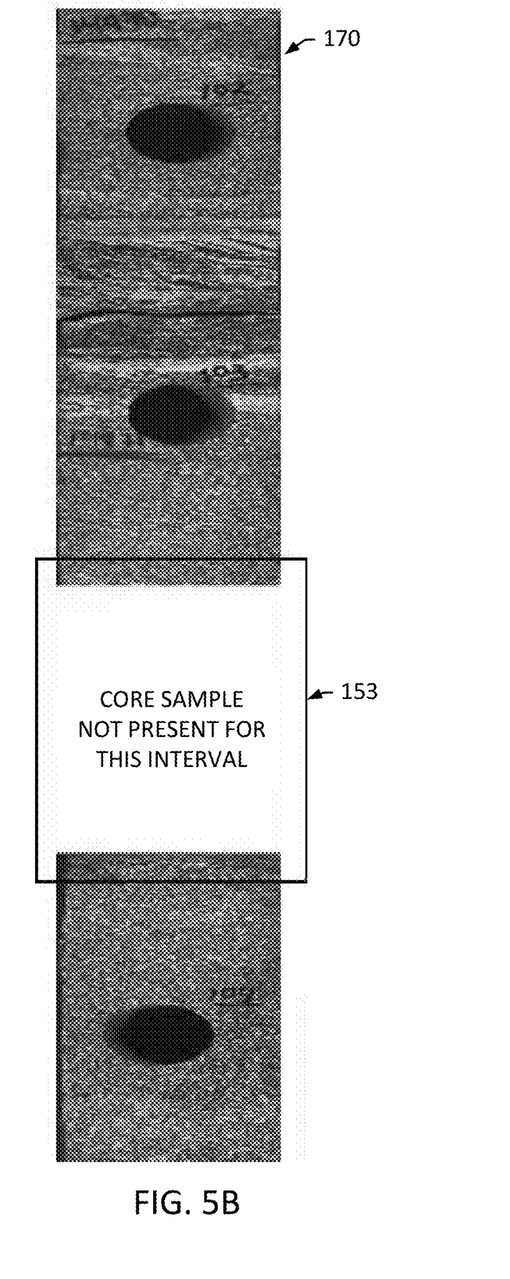

In some embodiments, laboratory assessment of a core 142 includes capturing images (for example, photographic images) of the core (or "core images") 170. FIGS. 4A-4C are diagrams that illustrate an example core 142 and a corresponding core image 170 in accordance with one or more embodiments. As illustrated in FIGS. 4A and 4B, the core 142 may be a solid cylindrical continuous section of rock of the formation 104. Continuing with the prior example, the core 142 may be determined to have a top core depth 400 (for example, a depth defined by the estimated in-situ location of an up-hole end 401 of the core 142) of about 100 m and a bottom core depth 402 (for example, a depth defined by the estimated in-situ location of a down-hole end 403 of the core 142) of about 105 m. In such an embodiment, the core 142 may be determined to have a core length of about 5 m and be associated with a core depth interval 404 of about 100 m to about 105 m. As illustrated in FIGS. 4A and 4B, the core 142 may be sliced along its longitudinal axis 406 (or "slapped") (as indicated by a cut-line 408) during a laboratory assessment to expose an internal cross-section (or "face") 410 of the core 142. During the laboratory assessment, the exposed face 410 of FIG. 4B (or the exterior of the core 142 of FIG. 4A) may be visually or physically assessed to identify various characteristics of the core 142. In some embodiments, a core image 170 includes a photographic image of the exposed face 410 (or the exterior) of the core 142. FIG. 4B is a diagram that illustrates a core image 170 depicting the exposed face 410 of the core 142 in accordance with one or more embodiments. The core image 170 includes depictions of multiple flaws 153 (153a-153c) present in the core 142. An upper (or "top") end 420 of the core image 170 may be associated with the top core depth 400 of about 100 m, and a lower (or "bottom") end 422 of the core image 170 may be associated with the bottom core depth 402 of about 105 m. The core image 170 may be associated with a core length of about 5 m and the core depth interval 404 of about 100 m to about 105 m (the depth interval associated with the portion of the core 142 represented by the core image 170). FIGS. 5A and 5B depict example core images 170 in accordance with one or more embodiments. The core image 170 of FIG. 5A depicts a flaw 153 defined by a dark band that extends across the core image 170. This may be, for example, a rubble zone that includes formation rock which was compacted during the coring operation. The core image 170 of FIG. 5B includes a flaw 153 defined by a white band (and text "Core Sample Not Present For this Interval") that extends across the core image 170. This may be, for example, a no recovery zone defined by an interval for which a core 142 has not been extracted or is otherwise not present. A core image 170 of a core 142 may be associated with a well number indicating the well from which the core 142 was extracted, a core number identifying the core 142 and a minimum depth and a maximum depth for that segment of the core 142.

Referring again to FIG. 1, in some embodiments, the control system 122 stores (or otherwise has access to) one or more well logs 152 for the well 106. As described, a well log 152 for the well 106 may reflect log data 154 obtained by way of a well logging of the wellbore 120 of the well 106. In some embodiments, the control system 122 stores (or otherwise has access to) one or more core logs 162 for the wellbore 120. A core log 162 for the well 106 may reflect core data 164 obtained by way of laboratory assessment of one or more cores 142 extracted from the wellbore 120 of the well 106. A core log 162 or its associated core data 164 may be used to directly assess characteristics of the formation 104 or may be compared to other data, such as log data 154, to verify or correct discrepancies within the core data 164. For example, in some embodiments, the core data 164 may be compared to log data 154 to identify offsets in the core depths associated with the core data 164, the core data 164 may be shifted to generate shifted core data 180 that accounts for the offsets, and the shifted core data 180 may be used to generate a shifted core log 190. In some embodiments, the core data 164 for a core 142 is segmented into multiple contiguous core segments defined by breaking points, and the contiguous core segments are iteratively assessed and shifted in sequence (for example, from the deepest contiguous core segment to the shallowest contiguous core segment) to align the core data 164 of the contiguous core segments with corresponding segments of log data 154. In some embodiments, for each shift of the core data 164 for an assessed contiguous core segment by a given distance, the core data 164 associated with all shallower contiguous core segments (if any) are also shifted by the given distance. In some embodiments, the breaking points used to define the contiguous core segments are identified based on image processing of a core image 170 of the core 142. The image processing may include, for example, identification and comparison of Haralick textual feature parameters for different portions of the core image 170.

Figure 6:
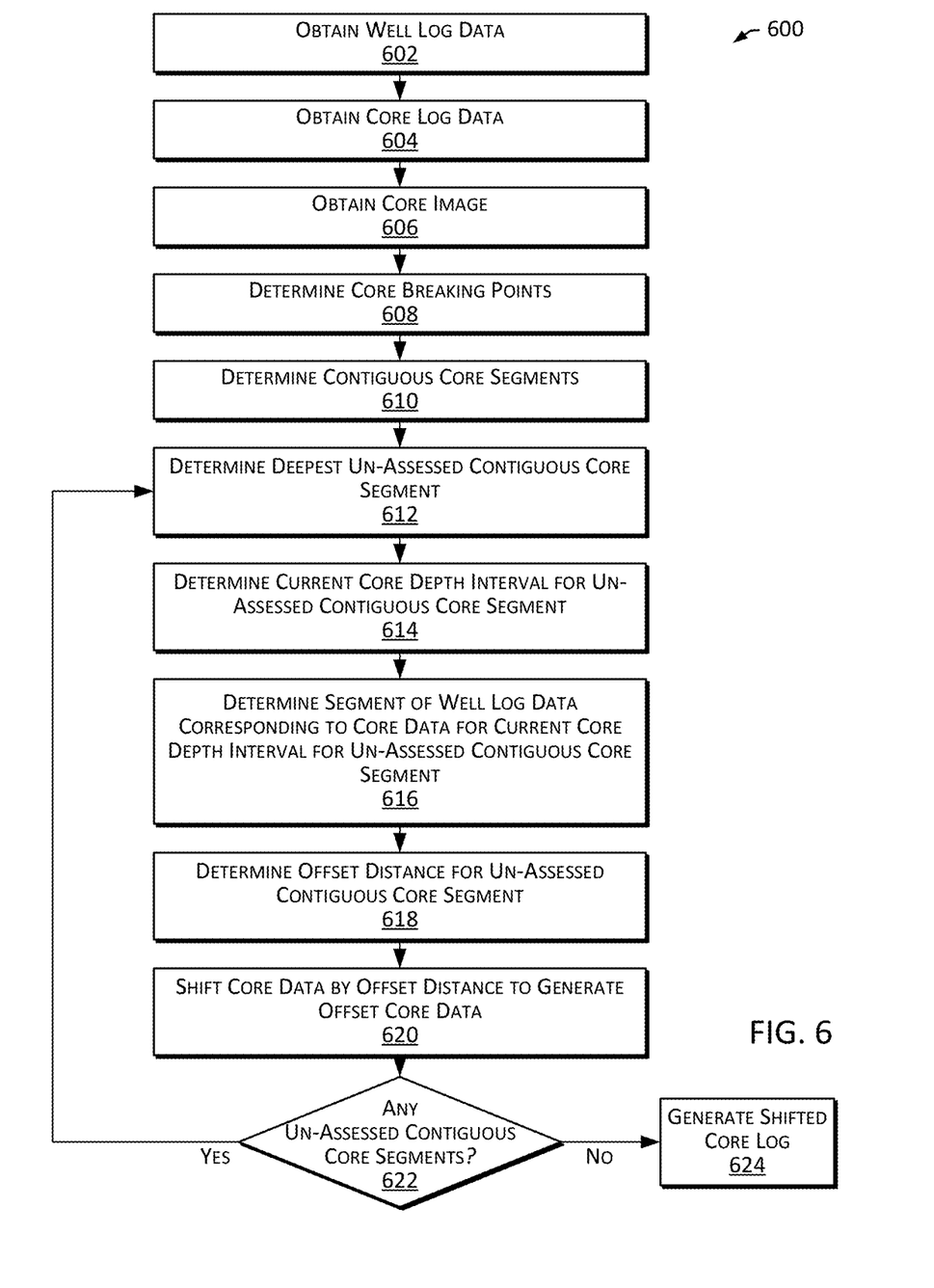
FIG. 6 is a flowchart that illustrates a method of core data shifting in accordance with one or more embodiments.

FIG. 6 is a flowchart that illustrates a method 600 of core data shifting in accordance with one or more embodiments. In the context of the well 106, the operational aspects of method 600 may be performed, for example, by the well control system 122 or another operator of the well 106.

In some embodiments, method 600 includes obtaining well log data (block 602). Obtaining well log data may include obtaining one or more well logs of a well. For example, obtaining well log data may include the well control system 122 (or another operator of the well 106) controlling operation of the well system 106 to conduct a logging operation to generate a well log 152 for the well 106 or the well control system 122 retrieving a well log 152 for the well 106 from computer memory. The well log 152 may include, for example, a porosity well log that identifies a porosity of the formation 104 surrounding the wellbore 120 versus measured depth in the wellbore 120 and which is determined based on log data 154 obtained by way of a logging of the wellbore 120 of the well 106. A well log 152 may be, for example, the well log 152 of FIG. 2, which includes log data 154 that identifies varying values of a characteristic (for example, porosity) of the formation 104 surrounding the wellbore 120 versus depth (for example, across a log depth interval of about 1000 m to about 1100 m) in the wellbore 120.

Referring again to FIG. 6, in some embodiments, method 600 includes obtaining core log data (block 604). Obtaining core log data may include obtaining one or more core logs of a well. For example, obtaining core log data may include the well control system 122 (or another operator of the well 106) controlling operation of the well system 106 to conduct a coring operation to extract one or more cores 142 (or to conduct a laboratory assessment of the one or more cores 142) to generate a core log 162 for the well 106 or the well control system 122 retrieving a core log 162 for the well 106 from computer memory. The core log 162 may include, for example, a porosity core log that identifies porosity of the formation 104 surrounding the wellbore 120 versus driller depth of the associated core 142 extracted from the wellbore 120 of the well 106 and which is determined based on core data 164 obtained by way of laboratory assessment of the core 142. A core log 162 may be, for example, the core log 162 of FIG. 3, which includes core data 164 that identifies varying values of a characteristic (for example, porosity) of the formation 104 surrounding the wellbore 120 versus depth (for example, across a core depth interval of about 1002 m to about 1092 m) in the wellbore 120.

Referring again to FIG. 6, in some embodiments, method 600 includes obtaining a core image (block 606). Obtaining a core image may include obtaining an image of one or more cores extracted from the wellbore of a well. For example, obtaining a core image may include the well control system 122 (or another operator of the well 106) controlling a laboratory assessment operation to capture a core image 170 of a core 142 extracted from the well 106 or the well control system 122 retrieving a core image 170 of the core 142 extracted from the well 106 from computer memory. The core image 170 may include, for example, a photographic image of the core 142. A core image 170 may be, for example, the core image 170 of FIG. 4C which illustrates a photographic image of the exposed face 410 of a core 142 which has a top end 420 associated with the top core depth 400 of about 1000 m and a bottom end 422 associated with the bottom core depth 402 of about 105 m, and which is associated with the core length of about 5 m and a core depth interval 404 of about 100 m to about 105 m.

Referring again to FIG. 6, in some embodiments, method 600 includes determining core breaking points (block 608). Determining core breaking points may include determining, based on a core image, one or more breaking points along a length of the core depicted by the core image. A breaking point may represent, for example, a flaw in the depicted core. Examples of flaws include a no recovery zone (for example, a location within the core that is missing physical pieces of the core) or a rubble zone (for example, a location within the core containing physical pieces of the core that are broken down into small fragments). A flaw may be represented in a core image by a white or black space (for example, a white or black line or zone) with or without text characterizing the associated flaw.

In some embodiments, determining core breaking points (or "breaking points") includes conducting image processing on a core image 170 of a core 142 to identify one or more breaking points along the length of the core 142 and a respective depth associated with each breaking point. For example, referring to FIG. 4C, determining core breaking points may include conducting image processing on the core image 170 to identify breaking points 450 (including breaking points 450a, 450b and 450c) associated with respective flaws 153 (including flaws 153a, 153b and 153c). In some embodiments, the image processing includes determining Haralick textual feature parameters for the core image 170. The Haralick textual feature parameters may include, for example, one, some or all of the following: (1) angular second moment; (2) contrast; (3) correlation; (4) sum of squares; (5) inverse difference moment; (6) sum average; (7) sum variance; (8) sum entropy; (9) entropy; (10) difference variance; (11) difference entropy; (12) and (13) information measures of correlation; and (14) maximal correlation coefficient. Examples of such processing is described in "Textural Features for Image Classification" by Robert M. Haralick, et. al. (1973), which is incorporated by reference. In some embodiments, one or more of these Haralick textual feature parameters are determined for a moving interval (or "window") of the core image 170, and the determined parameters are compared to predetermined conditions associated with breaking points to identify the breaking points 450. For example, referring to FIG. 4C, a value for each of the following Haralick textual feature parameters may be determined for each position of a 1 m interval (or "window") 452 as it is moved across the length of the core image 170 (for example, from the bottom end 422 of the core image 170 to the top end 420 of the core image 170, in 0.01 m increments, as illustrated by arrow 453: (1) angular second moment; (2) contrast; (5) inverse difference moment; (8) sum entropy; (9) entropy; (10) difference variance; (11) difference entropy; (13) information measure of correlation, and (14) maximal correlation coefficient. Breaking points 450 may be identified where the following conditions are satisfied: (1) angular second moment and (5) inverse difference moment have a value greater than a respective threshold (for example, each have their maximum values), and the other parameters have a value less than a respective threshold (for example, each have their minimum values). Breakpoints 450a, 450b and 450c may be identified, for example, at the core depths of 101 m, 103 m and 104 m, respectively, in response to determining that each of the identified parameters has a value that satisfies their respective thresholds at the core depths of 101 m, 103 m and 104 m. In some embodiments, the breaking points are identified when the following conditions are met for a specified interval (or "window") of the core image 170: (A) the value for parameters (1) and (5) are at the maximum compared to the rest of the windows, and (B) when the values for the parameters (2), (8), (9), (10), (11), (13) and (14) are the minimum compared to the rest of the intervals of the core image 170. All of the previous conditions may be met in order to identify this as a breaking point 450. That is, for example, if parameter (1) is not the maximum value for an interval, that interval will not be identified as a breaking point because one of the conditions has not been met.

Referring again to FIG. 6, in some embodiments, method 600 includes determining contiguous core segments (block 610). Determining contiguous core segments may include determining contiguous core segments based on the core breaking points determined. A contiguous core segment of a core 142 may include a segment of the core 142 located between adjacent breakpoints or between a breakpoint and an upper or lower end of the core 142 (or its core image 170). In some embodiments, determining contiguous core segments of a core 142 includes determining contiguous core segments that are each defined by depth interval bound by adjacent breakpoints 450 determined for the core 142 or between a breakpoint 450 and adjacent end of the core 142 (or its core image 170). Continuing with the example and referring to FIG. 4C, the core image 170 may be processed to identify breakpoints 450a, 450b and 450c and corresponding contiguous core segments 456a, 456b, 456c and 456d. In accordance with the breakpoints 450a, 450b and 450b being determined to occur at core depth intervals of about 100.9-101.1 m, 102.8-103.2 m and 103.9-104.1 m, respectively, the first contiguous core segment 456a may be determined to have a contiguous core segment top depth of about 100 m (which corresponds to the top core depth 400 of the core 142 and the top end 420 of the core image 170) and a contiguous core segment bottom depth of 100.9 m (which corresponds to the top depth of the first breakpoint 450a depth interval), the second contiguous core segment 456b may be determined to have a contiguous core segment top depth of 101.1 m (which corresponds to the bottom depth of the first breakpoint 450a depth interval) and a contiguous core segment bottom depth of about 102.8 m (which corresponds to the top depth of the second breakpoint 450b depth interval), the third contiguous core segment 456c may be determined to have a contiguous core segment top depth of about 103.2 m (which corresponds to the bottom depth of the second breakpoint 450b depth interval) and a contiguous core segment bottom depth of about 103.9 m (which corresponds to the top depth of the third breakpoint 450c depth interval), and the fourth contiguous core segment 456d may be determined to have a contiguous core segment top depth of about 104.1 m (which corresponds to the bottom depth of the third breakpoint 450c depth interval) and a contiguous core segment bottom depth of about 105 m (which corresponds to the bottom core depth 402 of the core 142 and the bottom end 422 of the core image 170). Accordingly, the contiguous core segments 456a, 456b, 456c and 456d may be defined by "initial" contiguous core segment depth intervals 458 (including contiguous core segment depth intervals 458a, 458b, 458c and 458d) of about 100 m-100.9 m, 101.1 m-102.8 m, 103.2 m-103.9 m and 104.1 m-105 m, respectively.

Referring again to FIG. 6, in some embodiments, method 600 includes determining a deepest un-assessed contiguous core segment (block 612). Determining a deepest un-assessed contiguous core segment may include identifying any contiguous core segments for which corresponding intervals of the core log data have not yet been assessed (for example, including the assessments described here with regard to blocks 614, 616, 618 and 620), and identifying, from any contiguous core segments identified, a contiguous core segment associated with the deepest contiguous core segment depth interval. In comparing two core segment depth intervals, a depth interval representing an interval closer to an up-hole end of a wellbore may be considered to be shallower than a depth interval representing an interval closer to a down-hole end of the wellbore. In some embodiments, determining a deepest un-assessed contiguous core segment for the well 106 may include identifying any contiguous core segments 456 for which corresponding intervals of the core log data 164 have not yet been assessed, and identifying, from any contiguous core segments 456 identified, the contiguous core segment 456 associated with the deepest contiguous core segment depth interval 458. Continuing with the example and referring to FIG. 4C, this may include the following: in a first iteration, identifying the contiguous core segment 456d from the contiguous core segments 456a, 456b, 456c and 456d; in a second iteration, identifying the contiguous core segment 456c from the contiguous core segments 456a, 456b and 456c; in a third iteration, identifying the contiguous core segment 456b from the contiguous core segments 456a and 456b; and in a fourth and final iteration, identifying the contiguous core segment 456a.

Referring again to FIG. 6, in some embodiments, method 600 includes determining a current core depth interval for the un-assessed contiguous core segment (block 614). Determining a current core depth interval for the un-assessed contiguous core segment may include determining a core depth interval currently associated with the contiguous core segment, including any prior shifting of the core depth interval for the contiguous core segment as a result of offsets determined (and associated shifting) in prior iterations. In some embodiments, determining a current core depth interval for an un-assessed contiguous core segment 456 includes determining a core depth interval 458 currently associated with the contiguous core segment 456, including any prior shifting of the core depth interval 458 for the contiguous core segment 456 as a result of offsets determined (and associated shifting) in prior iterations. Continuing with the example and referring to FIG. 4C, this may include the following: in a first iteration (for example, where no offsets have yet been determined and no shifts have yet occurred), determining a current core depth interval 458d of 104.1 m-105 m for the contiguous core segment 456d; in a second iteration (for example, where a 0.1 m upward (or "positive") offset has already been determined for the contiguous core segment 456d and a corresponding shift has already been applied to the core depth interval 458c of the contiguous core segment 456c), determining a current core depth interval of 103.1 m-103.8 m for the contiguous core segment 456c; in a third iteration (for example, where a 0.1 m and 0.2 m upward offsets have already been determined for the contiguous core segments 456d and 456c and corresponding shifts have already been applied to the core depth interval of the contiguous core segment 456b), determining a current core depth interval of 100.8 m-102.5 m for the contiguous core segment 456b; and in a fourth and final iteration (for example, where a 0.1 m, 0.2 m and 0.1 m upward offset have already been determined for the contiguous core segments 456d, 456c and 456d and corresponding shifts have already been applied to the core depth interval 458a of the contiguous core segment 456a), determining a current core depth interval of 99.6 m-100.5 m for the contiguous core segment 456a.

Referring again to FIG. 6, in some embodiments, method 600 includes determining a segment of the well log data corresponding to the current core depth interval for the un-assessed contiguous core segment (block 616). Determining a segment of the well log data corresponding to the current core depth interval for the un-assessed contiguous core segment may include determining a segment of the well log data corresponding to a depth interval that includes (and is slightly larger than) the depth interval for the un-assessed contiguous core segment. In some embodiments, determining a segment of the well log data 154 corresponding to the current core depth interval for an un-assessed contiguous core segment 456 includes determining a segment of the well log data 152 corresponding to a depth interval that includes and is slightly larger (for example, +/−a predetermined distance) than the depth interval for the un-assessed contiguous core segment 456. The predetermined distance may be about 5-15% of the length of the depth interval for the un-assessed contiguous core segment 456. The predetermined distance may be for example, about +/−0.1 m, +/−0.5 m, +/−1 m, +/−1.5 m, +/−5 m, or +/−10 m. For example, where the segment of the well log data 152 is predetermined to be +/−0.5 m larger than the depth interval 458 for the un-assessed contiguous core segment 456, in the first, second, third and fourth iterations, the segment of the well log data 152 may be the well log data 152 corresponding to the log depth intervals of 103.6 m-105.5 m, 102.6 m-104.3 m, 100.3 m-103.0 m, and 99.1 m-101.0 m, respectively. Such an oversizing of the log depth interval may help to assure that the log depth interval contains a segment of log data 154 that correspond to the segment of the core data 164 associated with the depth interval for the un-assessed contiguous core segment 456.

In some embodiments, method 600 includes determining an offset distance for the un-assessed contiguous core segment (block 618). Determining an offset distance for the un-assessed contiguous core segment may include correlating a segment of the core data corresponding to the current core depth interval for the un-assessed contiguous core segment with the segment of the well log data corresponding to the current core depth interval for the un-assessed contiguous core segment to determine an offset distance between the two. In some embodiments, determining an offset distance for an un-assessed contiguous core segment 456 may include correlating a segment of the core data 164 corresponding to the current core depth interval 458 for the un-assessed contiguous core segment 456 with the segment of the well log data 154 corresponding to the current core depth interval 458 for the un-assessed contiguous core segment 456, to determine an offset distance (OD) between the two. For example, in a first iteration, the comparing the core data 164 corresponding to the core depth interval of 104.1 m-105 m to the well log data 152 corresponding to the depth intervals of 103.6 m-105.5 m to determine that the segment of the core data 164 corresponding to the core depth interval of 104.1 m-105 m correlates to a segment of the well log data 154 corresponding to a log depth interval of 104.0 m-104.9 m, and determining an offset distance (OD) of 0.1 m (which corresponds to the distance between the core depth interval and the depth interval determined to correlate to the data for the core depth interval). A similar correlation maybe performed in each iteration of the assessment of the contiguous core segment 456c, 456b and 456a to determine a corresponding offset for each of the contiguous core segment 456c, 456b and 456a.

In some embodiments, correlating a segment of the core data 164 corresponding to the current core depth interval 458 for the un-assessed contiguous core segment 456 with the segment of the well log data 154 corresponding to the current core depth interval 458 includes correlating the core data 164 corresponding to the current core depth interval 458 with corresponding contiguous segments of the log data 154 for the segment of the well log data 154 corresponding to the current core depth interval 458, and selecting the best/strongest correlation of the correlations. For example, with regard to the contiguous core segment 458d, in a first iteration of the correlation, the core data 164 for depth 104.1 m to 105 m (for example, having nine data points in that range) may be correlated with well log data 152 for the depth interval 104.6 m-105.5 m (for example, the "bottom" nine data points in the segment of the well log data 154 corresponding to the core depth interval 458d), in a second iteration of the correlation, the core data 164 for the depth interval 104.1 m to 105 m may be correlated with well log data 152 for the depth 104.5 m-105.4 m (for example, the next higher set of nine data points in the segment of the well log data 154 corresponding to the core depth interval 458d), and so forth until the "top" nine data points in the segment of the well log data 154 (for example, the well log data 154 for the depth 103.6 m to 104.5 m) are correlated. Then, the correlation with the maximum correlation coefficient (for example, the correlation to the well log data 154 for 104.0 m to 104.9 m) may be selected as the correlation of the core data 164 for depth 104.1 m to 105 m. The offset (or "shift") distance may be determined based on the difference between the top depths of the depth intervals for the core data 164 and the correlated well log data 154 (for example, offset distance=104.1 m-104.0 m=0.1 m). The correlation of corresponding data sets may employ a Pearson Correlation function.

In some embodiments, method 600 includes shifting the core data by the offset distance to generate offset (or "shifted core data") core data (block 620). Shifting the core data by the offset distance may include for each iteration of an assessment of a given contiguous core segment, shifting the core data associated with the given contiguous core segment, and the core data associated with any contiguous core segments that are shallower than the given contiguous core segment, by the offset distance. This may include shifting the current core depth interval 458 associated with the given contiguous core segment 456, and the current core depth intervals 458 of any contiguous core segments 456 that are shallower than the given contiguous core segment 456, by the offset distance to generate shifted core data 180. For example, continuing with the example, in a first iteration (where a 0.1 m of upward (or "positive") offset has been determined for the contiguous core segment 456d), the current core depth interval 458d (104.1 m-105 m) associated with the contiguous core segment 456d and the current core depth intervals 458c, 458b and 458a of the contiguous core segments 456c, 456b and 456a (which are all of the contiguous core segments 456 shallower than the contiguous core segment 456d) may be shifted upward by the determined offset distance of 0.1 m such that the core depth intervals 458d, 458c, 458b and 458a for the contiguous core segments 456d, 456c, 456b and 456a are 104.0 m-104.9 m, 103.1 m-103.8 m, 101.0 m-102.7 m, and 99.9 m-100.8 m, respectively. In a second iteration (where a 0.2 m upward offset has been determined for the contiguous core segment 456c), the current core depth interval 458c (103.1 m-103.8 m) associated with the contiguous core segment 456c and the current core depth intervals 458b and 458a of the contiguous core segments 456b and 456a (which are all of the contiguous core segments 456 shallower than the contiguous core segment 456c) may be further shifted upward by the determined offset distance of 0.2 m such that the core depth intervals 458d, 458c, 458b and 458a for the contiguous core segments 456d, 456c, 456b and 456a are 104.0 m-104.9 m, 102.9 m-103.6 m, 100.8 m-102.5 m, and 99.7 m-100.6 m, respectively. A similar shift may be applied in each of the iterations of assessment of the contiguous core segments 456b and 456a to determine the "shifted" core depth intervals 458d, 458c, 458b and 458a for the contiguous core segments 456d, 456c, 456b and 456a to be 104.0 m-104.9 m, 102.9 m-103.6 m, 100.7 m-102.4 m, and 99.6 m-100.5 m, respectively (for example, where the contiguous core segments 456a and 45b are each determined to have a 0.1 m offset distance). The shifted core data 180 may include the characteristic values of the respective subsets of core data 164 associated with the contiguous core segments 456 being associated with the respective "shifted" core depth intervals 458. For example, the shifted core data 180 may include the characteristic values of the respective subsets of core data 164 associated with the contiguous core segments 456d, 456c, 456b and 456a being associated with the respective "current" shifted core depth intervals 458d, 458c, 458b and 458a of 104.0 m-104.9 m, 102.9 m-103.6 m, 100.7 m-102.4 m, and 99.5 m-100.4 m.

Figure 7:
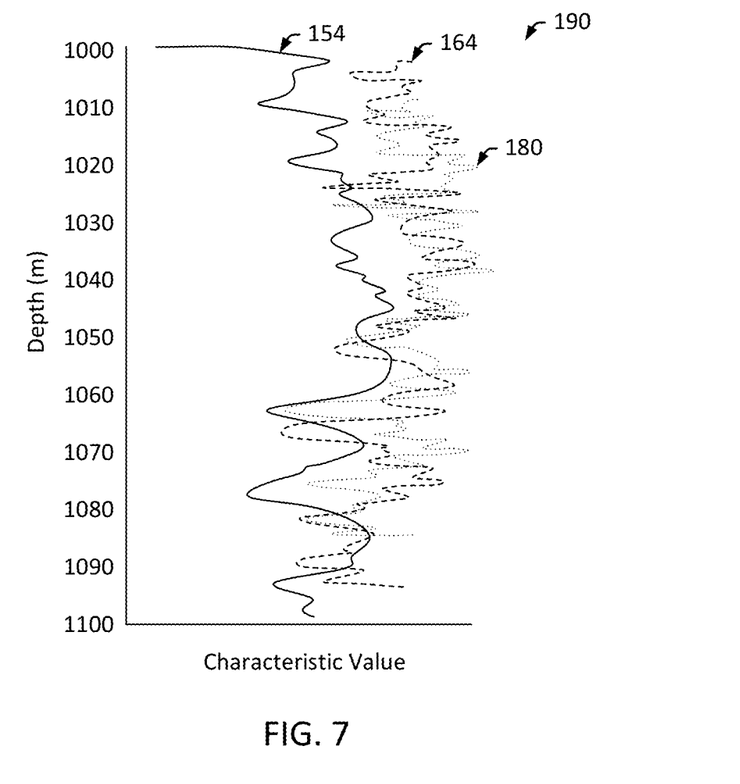
FIG. 7 is a diagram that illustrates log data, core data and shifted core data in accordance with one or more embodiments.

In some embodiments, method 600 includes determining any un-assessed contiguous core segments (block 622). Determining any un-assessed contiguous core segments may include whether any of the contiguous core segments have not yet been assessed (for example, to determine and apply an offset distance (if any) as described at block 612-620). In response to determining that any of the contiguous core segments have not yet been assessed, the method may return to determining and assessing the deepest of the un-assessed contiguous core segments (blocks 612-620). For example, in a first iteration (where the "deepest" contiguous core segment 456d has just been assessed), it may be determined that the contiguous core segments 456c, 456b and 456a remain unassessed, and method 600 may proceed to identifying and assessing the contiguous core segment 456c (which is the next/adjacent contiguous core segment 456 shallower than the contiguous core segment 456d). In response to determining that all of the contiguous core segments have been assessed (that is, none of the contiguous core segments have not yet been assessed), method 600 may proceed to generating a shifted core log (block 624). For example, in a fourth and final iteration (where the "shallowest" contiguous core segment 456a has just been assessed), it may be determined that all of the contiguous core segments 456 have been assessed, and method 600 may proceed to generating a shifted core log 190 based on the shifted core data 180. A shifted core log 190 may include a core log that reflects the shifts in the depth intervals associated with the core data 164. For example, a shifted core log 190 may include a record of the values of the characteristic (for example, porosity) of the respective subsets of core data 164 associated with the contiguous core segments 456d, 456c, 456b and 456a as a function of depth, based on the "current" shifted core depth intervals 458d, 458c, 458b and 458a of 104.0 m-104.9 m, 102.9 m-103.6 m, 100.7 m-102.4 m, and 99.5 m-100.4 m associated with the contiguous core segments 456d, 456c, 456b and 456a, respectively. FIG. 7 is a diagram that illustrates a shifted core log 190 in accordance with one or more embodiments. In the illustrated embodiment, the shifted core log 190 depicts shifted core log data 180. The associated log data 154 and the original (un-shifted) core data 164 (based on "driller depths" or "un-shifted core depths") are provided for comparison. Notably, the shifted core log data 180 aligns more closely with the associated log data 154 than the original (un-shifted) core data 164.

In some embodiments, a reservoir is developed based on shifted core log data. This may include defining or conducting various operations for development of the reservoir 102 based on the shifted core log data 180 or the shifted core log 190. For example, the control system 122 (or another operator of the reservoir 102) may determine, based on the shifted core log data 180 or the shifted core log 190, drilling parameters (for example, well locations and trajectories) or operating parameters (for example, production rates and pressures or injection rates and pressure) for the well 106 (or other wells in the reservoir 102), or may control drilling or operation of the well 106 (or other wells in the reservoir 102) in accordance with the drilling or operating parameters (for example, to drill a well at a determined location or having a determined trajectory, or to operate a well at a determined rate or pressure). In some embodiments, development of a reservoir based on shifted core log data includes generating a model of the reservoir (or "reservoir model") based on the shifted core log. For example, the control system 122 (or another operator of the reservoir 102) may determine, based on the shifted core log data 180 or the shifted core log 190, a three-dimensional model of the reservoir 102. The model may be used for example to assess the current state of the reservoir 102, to predict a future state of the reservoir 102, or to determine actions to be taken to develop the reservoir 102. In some embodiments, the drilling or operating parameters for the well 106 (or other wells in the reservoir 102) may be determined based on the model.

Figure 8:
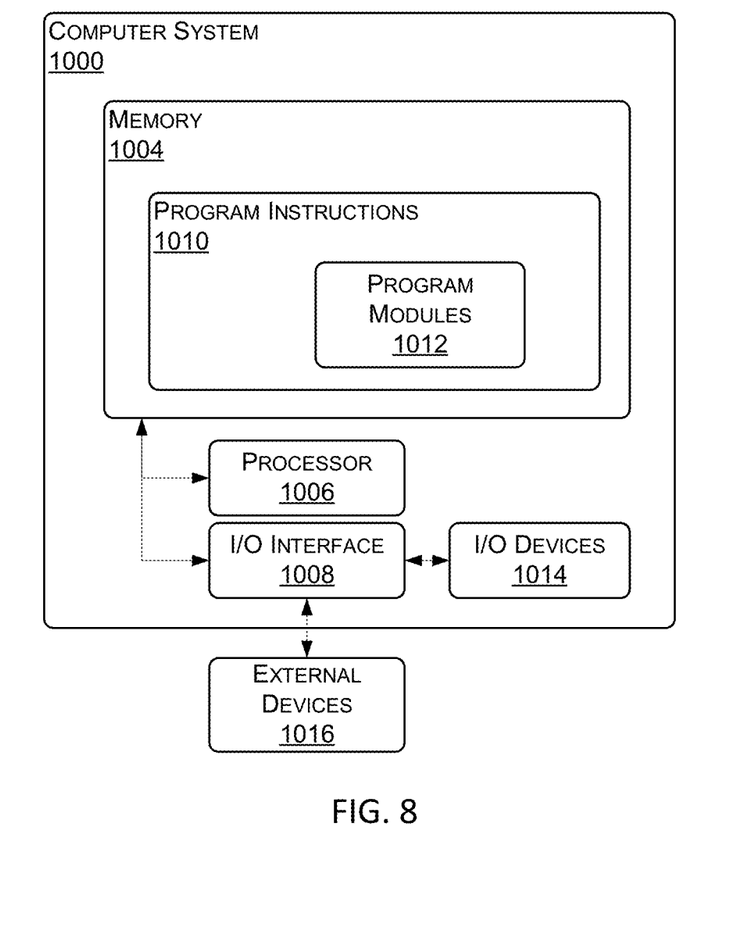
FIG. 8 is a diagram that illustrates an example computer system in accordance with one or more embodiments.

FIG. 8 is a diagram that illustrates an example computer system (or "system") 1000 in accordance with one or more embodiments. In some embodiments, the system 1000 is a programmable logic controller (PLC). The system 1000 may include a memory 1004, a processor 1006 and an input/output (I/O) interface 1008. The memory 1004 may include non-volatile memory (for example, flash memory, read-only memory (ROM), programmable read-only memory (PROM), erasable programmable read-only memory (EPROM), electrically erasable programmable read-only memory (EEPROM)), volatile memory (for example, random access memory (RAM), static random access memory (SRAM), synchronous dynamic RAM (SDRAM)), or bulk storage memory (for example, CD-ROM or DVD-ROM, hard drives). The memory 1004 may include a non-transitory computer-readable storage medium having program instructions 1010 stored thereon. The program instructions 1010 may include program modules 1012 that are executable by a computer processor (for example, the processor 1006) to cause the functional operations described, such as those described with regard to the well control system 122 (or another operator of the well 106) or the method 600.

The processor 1006 may be any suitable processor capable of executing program instructions. The processor 1006 may include a central processing unit (CPU) that carries out program instructions (for example, the program instructions of the program modules 1012) to perform the arithmetical, logical, or input/output operations described. The processor 1006 may include one or more processors. The I/O interface 1008 may provide an interface for communication with one or more I/O devices 1014, such as a joystick, a computer mouse, a keyboard, or a display screen (for example, an electronic display for displaying a graphical user interface (GUI)). The I/O devices 1014 may include one or more of the user input devices. The I/O devices 1014 may be connected to the I/O interface 1008 by way of a wired connection (for example, an Industrial Ethernet connection) or a wireless connection (for example, a Wi-Fi connection). The I/O interface 1008 may provide an interface for communication with one or more external devices 1016. In some embodiments, the I/O interface 1008 includes one or both of an antenna and a transceiver. In some embodiments, the external devices 1016 include the well drilling system 130.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described here are to be taken as examples of embodiments. Elements and materials may be substituted for those illustrated and described here, parts and processes may be reversed or omitted, and certain features of the embodiments may be utilized independently, all as would be apparent to one skilled in the art after having the benefit of this description of the embodiments. Changes may be made in the elements described here without departing from the spirit and scope of the embodiments as described in the following claims. Headings used here are for organizational purposes only and are not meant to be used to limit the scope of the description.

It will be appreciated that the processes and methods described here are example embodiments of processes and methods that may be employed in accordance with the techniques described here. The processes and methods may be modified to facilitate variations of their implementation and use. The order of the processes and methods and the operations provided may be changed, and various elements may be added, reordered, combined, omitted, modified, and so forth. Portions of the processes and methods may be implemented in software, hardware, or a combination of software and hardware. Some or all of the portions of the processes and methods may be implemented by one or more of the processors/modules/applications described here.

As used throughout this application, the word "may" is used in a permissive sense (that is, meaning having the potential to), rather than the mandatory sense (that is, meaning must). The words "include," "including," and "includes" mean including, but not limited to. As used throughout this application, the singular forms "a", "an," and "the" include plural referents unless the content clearly indicates otherwise. Thus, for example, reference to "an element" may include a combination of two or more elements. As used throughout this application, the term "or" is used in an inclusive sense, unless indicated otherwise. That is, a description of an element including A or B may refer to the element including one or both of A and B. As used throughout this application, the phrase "based on" does not limit the associated operation to being solely based on a particular item. Thus, for example, processing "based on" data A may include processing based at least in part on data A and based at least in part on data B, unless the content clearly indicates otherwise. As used throughout this application, the term "from" does not limit the associated operation to being directly from. Thus, for example, receiving an item "from" an entity may include receiving an item directly from the entity or indirectly from the entity (for example, by way of an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

What is claimed is:

1. A method of core data shifting, the method comprising:
   obtaining a core image representing a length of a core extracted from a wellbore of a well extending into a formation, the core comprising a sample of rock of the formation extracted from the wellbore;
   determining, based on the core image, breaking points along the length of the core, each of the breaking points defining a location of a flaw within the core;
   determining, based on the breaking points, contiguous core segments of the core;
   determining, for each of the contiguous core segments of the core, a core depth interval for the contiguous core segment;
   generating, based on the contiguous core segments of the core, a shifted core-log, the generating of the shifted core-log comprising iteratively assessing each of the contiguous core segments in series from the contiguous core segment associated with a deepest core depth interval to the contiguous core segment associated with a shallowest core depth interval, the assessment of each of the contiguous core segments comprising:
      determining a current core depth interval for the contiguous core segment, the core depth interval for the contiguous core segment comprising the core depth interval currently associated with the contiguous core segment;
      correlating the core data for the contiguous core segment to log data for a log depth interval corresponding to the core depth interval currently associated with the contiguous core segment to identify a segment of the log data corresponding to the core data for the contiguous core segment;
      determining, based on the segment of the log data identified, an offset distance for the contiguous core segment, the offset distance for the contiguous core segment comprising an offset distance between the core depth interval for the contiguous core segment and the log depth interval associated with the segment of the log data identified;
      determining, based on the offset distance for the contiguous core segment, a shifted core depth interval for the contiguous core segment, the shifted core depth interval corresponding to a shift of the core depth interval currently associated with the contiguous core segment by the offset distance for the contiguous core segment; and
      for each of the contiguous core segments having a core depth interval that is associated with depths shallower than the core depth interval of the contiguous core segment, shifting the core depth interval associated with the contiguous core segment by the offset distance;

the shifted core-log associating core data for each contiguous core segment of the contiguous core segments with the shifted depth interval determined for the contiguous core segment.

2. The method of claim 1, wherein each of the flaws corresponds to a no recovery zone or a rubble zone within the core.

3. The method of claim 1, wherein determining breaking points along the length of the core comprises comparison of Haralick textual feature parameters across different portions of the core image.

4. The method of claim 1, wherein a beginning or end of each of the contiguous core segments is defined by one of the breaking points.

5. The method of claim 1, wherein the log depth interval corresponding to the core depth interval comprises a depth interval that includes and is larger than the core depth interval.

6. The method of claim 1, further comprising developing a reservoir in the formation based on the shifted core-log.

7. The method of claim 6, wherein developing the reservoir in the formation based on the shifted core-log comprises identifying operating parameters for the hydrocarbon well based on the shifted core-log, and operating the well in accordance with the operating parameters.

8. The method of claim 6, wherein developing the reservoir in the formation based on the shifted core-log comprises generating a model of the reservoir based on the shifted core-log.

9. A hydrocarbon well drilling system, comprising:
a drilling system configured to extract a core from a wellbore of a well extending into a formation, the core comprising a sample of rock of the formation; and
a well control system configured to perform the following operations:
obtain a core image representing a length of the core;
determine, based on the core image, breaking points along the length of the core, each of the breaking points defining a location of a flaw within the core;
determine, based on the breaking points, contiguous core segments of the core;
determine, for each of the contiguous core segments of the core, a core depth interval for the contiguous core segment;
generate, based on the contiguous core segments of the core, a shifted core-log, the generating of the shifted core-log comprising iteratively assessing each of the contiguous core segments in series from the contiguous core segment associated with a deepest core depth interval to the contiguous core segment associated with a shallowest core depth interval, the assessment of each of the contiguous core segments comprising:
determining a current core depth interval for the contiguous core segment, the core depth interval for the contiguous core segment comprising the core depth interval currently associated with the contiguous core segment;
correlating the core data for the contiguous core segment to log data for a log depth interval corresponding to the core depth interval currently associated with the contiguous core segment to identify a segment of the log data corresponding to the core data for the contiguous core segment;
determining, based on the segment of the log data identified, an offset distance for the contiguous core segment, the offset distance for the contiguous core segment comprising an offset distance between the core depth interval for the contiguous core segment and the log depth interval associated with the segment of the log data identified;
determining, based on the offset distance for the contiguous core segment, a shifted core depth interval for the contiguous core segment, the shifted core depth interval corresponding to a shift of the core depth interval currently associated with the contiguous core segment by the offset distance for the contiguous core segment; and
for each of the contiguous core segments having a core depth interval that is associated with depths shallower than the core depth interval of the contiguous core segment, shifting the core depth interval associated with the contiguous core segment by the offset distance;
the shifted core-log associating core data for each contiguous core segment of the contiguous core segments with the shifted depth interval determined for the contiguous core segment.

10. The system of claim 9, wherein each of the flaws corresponds to a no recovery zone or a rubble zone within the core.

11. The system of claim 9, wherein determining breaking points along the length of the core comprises comparison of Haralick textual feature parameters across different portions of the core image.

12. The system of claim 9, wherein a beginning or end of each of the contiguous core segments is defined by one of the breaking points.

13. The system of claim 9, wherein the log depth interval corresponding to the core depth interval comprises a depth interval that includes and is larger than the core depth interval.

14. The system of claim 9, the operations further comprising developing a reservoir in the formation based on the shifted core-log.

15. The system of claim 14, wherein developing the reservoir in the formation based on the shifted core-log comprises identifying operating parameters for the hydrocarbon well based on the shifted core-log, and operating the well in accordance with the operating parameters.

16. The system of claim 14, wherein developing the reservoir in the formation based on the shifted core-log comprises generating a model of the reservoir based on the shifted core-log.

17. A non-transitory computer readable storage medium comprising program instructions stored thereon that are executable by a processor to perform the following operations for core data shifting:
obtaining a core image representing a length of a core extracted from a wellbore of a well extending into a formation, the core comprising a sample of rock of the formation;
determining, based on the core image, breaking points along the length of the core, each of the breaking points defining a location of a flaw within the core;
determining, based on the breaking points, contiguous core segments of the core;
determining, for each of the contiguous core segments of the core, a core depth interval for the contiguous core segment;

generating, based on the contiguous core segments of the core, a shifted core-log, the generating of the shifted core-log comprising iteratively assessing each of the contiguous core segments in series from the contiguous core segment associated with a deepest core depth interval to the contiguous core segment associated with a shallowest core depth interval, the assessment of each of the contiguous core segments comprising:

determining a current core depth interval for the contiguous core segment, the core depth interval for the contiguous core segment comprising the core depth interval currently associated with the contiguous core segment;

correlating the core data for the contiguous core segment to log data for a log depth interval corresponding to the core depth interval currently associated with the contiguous core segment to identify a segment of the log data corresponding to the core data for the contiguous core segment;

determining, based on the segment of the log data identified, an offset distance for the contiguous core segment, the offset distance for the contiguous core segment comprising an offset distance between the core depth interval for the contiguous core segment and the log depth interval associated with the segment of the log data identified;

determining, based on the offset distance for the contiguous core segment, a shifted core depth interval for the contiguous core segment, the shifted core depth interval corresponding to a shift of the core depth interval currently associated with the contiguous core segment by the offset distance for the contiguous core segment; and for each of the contiguous core segments having a core depth interval that is associated with depths shallower than the core depth interval of the contiguous core segment, shifting the core depth interval associated with the contiguous core segment by the offset distance;

the shifted core-log associating core data for each contiguous core segment of the contiguous core segments with the shifted depth interval determined for the contiguous core segment.

18. The medium of claim 17, wherein each of the flaws corresponds to a no recovery zone or a rubble zone within the core.

19. The medium of claim 17, wherein determining breaking points along the length of the core comprises comparison of Haralick textual feature parameters across different portions of the core image.

20. The medium of claim 17, wherein a beginning or end of each of the contiguous core segments is defined by one of the breaking points.

21. The medium of claim 17, wherein the log depth interval corresponding to the core depth interval comprises a depth interval that includes and is larger than the core depth interval.

22. The medium of claim 17, the operations further comprising developing a reservoir in the formation based on the shifted core-log.

23. The medium of claim 22, wherein developing the reservoir in the formation based on the shifted core-log comprises identifying operating parameters for the hydrocarbon well based on the shifted core-log, and operating the well in accordance with the operating parameters.

24. The medium of claim 22, wherein developing the reservoir in the formation based on the shifted core-log comprises generating a model of the reservoir based on based on the shifted core-log.

* * * * *